(12) United States Patent
Burbank et al.

(10) Patent No.: US 7,229,439 B2
(45) Date of Patent: Jun. 12, 2007

(54) APPARATUS AND METHOD FOR ACCESSING A BODY SITE

(75) Inventors: Fred H. Burbank, Laguna Niguel, CA (US); Paul Lubock, Laguna Niguel, CA (US); Martin Shabaz, Lake Forest, CA (US); Frank Louw, Carlsbad, CA (US)

(73) Assignee: Senorx, Inc., Aliso Viejo, CA (US)

( * ) Notice: Subject to any disclaimer, the term of this patent is extended or adjusted under 35 U.S.C. 154(b) by 92 days.

(21) Appl. No.: 10/851,342

(22) Filed: May 21, 2004

(65) Prior Publication Data

US 2004/0215187 A1    Oct. 28, 2004

Related U.S. Application Data

(63) Continuation of application No. 10/179,933, filed on Jun. 21, 2002, now Pat. No. 6,758,848, which is a continuation-in-part of application No. 09/717,176, filed on Nov. 16, 2000, now Pat. No. 6,497,706.

(51) Int. Cl.
  *A61F 18/18* (2006.01)
(52) U.S. Cl. .................. 606/45; 606/170; 606/171
(58) Field of Classification Search .............. 606/41, 606/45, 46–48, 170, 171; 600/564–568
See application file for complete search history.

(56) References Cited

U.S. PATENT DOCUMENTS

| 2,032,860 | A | 3/1936 | Wappler et al. |
| 2,192,270 | A | 3/1940 | McGowan |
| 3,341,417 | A | 9/1967 | Sinaiko |

(Continued)

FOREIGN PATENT DOCUMENTS

DE    12 25 813    9/1966

(Continued)

OTHER PUBLICATIONS

Armstrong, J. S., et al., "Differential marking of Excision Planes in Screened Breast lesions By Organically Coloured Gelatins", *Journal of Clinical Pathology*, Jul. 1990, No. 43 (7) pp. 604-607, XP000971447 abstract; tables 1,2.

(Continued)

*Primary Examiner*—Roy D. Gibson
(74) *Attorney, Agent, or Firm*—Edward J. Lynch; Duane Morris LLP

(57) ABSTRACT

A device and method of using the device to access a desired tissue site within a patient's body and separating a tissue specimen from the tissue site suitable for evaluation. The device includes a probe member having an arcuate tissue-cutting RF powered electrode secured to and distally spaced from the distal end of the probe and a small dimensioned distal extremity which when an inner lumen thereof is subjected to a vacuum, secured tissue for the specimen to the surface of the distal extremity. A circular tissue-cutting blade preferably secured to the distal end of a supporting tube is configured to rotate and move longitudinally along the shaft of the probe member effective to sever a tissue specimen from tissue secured to the surface of the distal extremity of the probe member. The supporting tube covers the separated specimen, and may be disposed within an accessing cannula.

17 Claims, 13 Drawing Sheets

U.S. PATENT DOCUMENTS

| | | | |
|---|---|---|---|
| 3,805,791 A | 4/1974 | Seuberth et al. | |
| 3,818,894 A | 6/1974 | Wichterle et al. | |
| 3,823,212 A | 7/1974 | Chvapil | |
| 3,945,375 A | 3/1976 | Banko et al. | |
| 3,955,578 A | 5/1976 | Chamness et al. | |
| 4,007,732 A | 2/1977 | Kvavle et al. | |
| 4,172,449 A | 10/1979 | LeRoy et al. | |
| 4,197,846 A | 4/1980 | Bucalo | |
| 4,202,338 A | 5/1980 | Bitrolf | |
| 4,243,048 A | 1/1981 | Griffin | |
| 4,276,885 A | 7/1981 | Tickner et al. | |
| 4,294,241 A | 10/1981 | Miyata | |
| 4,294,254 A | 10/1981 | Chamness | |
| 4,311,143 A | 1/1982 | Komiya | |
| 4,331,654 A | 5/1982 | Morris | |
| 4,362,160 A | 12/1982 | Hiltebrandt | |
| 4,503,855 A | 3/1985 | Maslanka | |
| 4,545,367 A | 10/1985 | Tucci | |
| 4,565,200 A | 1/1986 | Cosman | |
| 4,576,162 A | 3/1986 | McCorkle | |
| 4,638,802 A | 1/1987 | Okada | |
| 4,647,480 A | 3/1987 | Ahmed | |
| 4,693,237 A | 9/1987 | Hoffman et al. | |
| 4,718,419 A | 1/1988 | Okada | |
| 4,724,836 A | 2/1988 | Okada | |
| 4,813,062 A | 3/1989 | Gilpatrick | |
| 4,847,049 A | 7/1989 | Yamamoto | |
| 4,863,470 A | 9/1989 | Carter | |
| 4,909,250 A | 3/1990 | Smith | |
| 4,926,858 A | 5/1990 | Gifford, III et al. | |
| 5,007,908 A | 4/1991 | Rydell | |
| 5,024,617 A | 6/1991 | Karpiel | |
| 5,035,696 A | 7/1991 | Rydell | |
| 5,041,124 A | 8/1991 | Kensey | |
| 5,047,027 A | 9/1991 | Rydell | |
| 5,064,424 A | 11/1991 | Bitrolf | |
| 5,066,295 A | 11/1991 | Kozak et al. | |
| 5,078,716 A | 1/1992 | Doll | |
| 5,080,660 A | 1/1992 | Buelna | |
| 5,085,659 A | 2/1992 | Rydell | |
| RE33,925 E | 5/1992 | Bales et al. | |
| 5,133,359 A | 7/1992 | Kedem | |
| RE34,056 E | 9/1992 | Lindgren et al. | |
| 5,147,307 A | 9/1992 | Gluck | |
| 5,158,561 A | 10/1992 | Rydell et al. | |
| 5,163,938 A | 11/1992 | Kambara et al. | |
| 5,195,533 A | 3/1993 | Chin et al. | |
| 5,196,007 A | 3/1993 | Ellman et al. | |
| 5,201,732 A | 4/1993 | Parins et al. | |
| 5,201,741 A | 4/1993 | Dulebohn | |
| 5,207,686 A | 5/1993 | Dolgin | |
| 5,224,488 A | 7/1993 | Neuffer | |
| 5,236,410 A | 8/1993 | Granov et al. | |
| 5,281,218 A | 1/1994 | Imran | |
| 5,281,408 A | 1/1994 | Unger | |
| 5,282,781 A | 2/1994 | Liprie | |
| 5,312,400 A | 5/1994 | Bales et al. | |
| 5,318,564 A | 6/1994 | Eggers | |
| 5,323,768 A | 6/1994 | Saito et al. | |
| 5,324,288 A | 6/1994 | Billings et al. | |
| 5,334,381 A | 8/1994 | Unger | |
| 5,335,671 A | 8/1994 | Clement | |
| 5,344,420 A | 9/1994 | Hilal et al. | |
| 5,368,030 A | 11/1994 | Zinreich et al. | |
| 5,376,094 A | 12/1994 | Kline | |
| 5,380,321 A | 1/1995 | Yoon | |
| 5,395,312 A | 3/1995 | Desai | |
| 5,395,319 A | 3/1995 | Hirsch et al. | |
| 5,415,656 A | 5/1995 | Tihon et al. | |
| 5,417,687 A | 5/1995 | Nardella et al. | |
| 5,417,697 A | 5/1995 | Wilk et al. | |
| 5,422,730 A | 6/1995 | Barlow et al. | |
| 5,423,814 A | 6/1995 | Zhu et al. | |
| 5,431,649 A | 7/1995 | Mulier et al. | |
| 5,433,204 A | 7/1995 | Olson | |
| 5,437,665 A | 8/1995 | Munro | |
| 5,441,503 A | 8/1995 | Considine et al. | |
| 5,462,553 A | 10/1995 | Dolgin | |
| 5,470,308 A | 11/1995 | Edwards et al. | |
| 5,484,436 A | 1/1996 | Eggers et al. | |
| 5,487,385 A | 1/1996 | Avitall | |
| 5,494,030 A | 2/1996 | Swartz et al. | |
| 5,501,654 A | 3/1996 | Failla et al. | |
| 5,526,822 A | 6/1996 | Burbank et al. | |
| 5,527,331 A | 6/1996 | Dresch et al. | |
| 5,527,332 A | 6/1996 | Clement | |
| 5,538,010 A | 7/1996 | Darr et al. | |
| 5,542,948 A | 8/1996 | Weaver et al. | |
| 5,549,560 A | 8/1996 | Van de Wijdeven | |
| 5,595,185 A | 1/1997 | Erlich et al. | |
| 5,607,389 A | 3/1997 | Edwards et al. | |
| 5,611,803 A | 3/1997 | Heaven et al. | |
| 5,636,255 A | 6/1997 | Ellis | |
| 5,643,246 A | 7/1997 | Leeb et al. | |
| 5,643,282 A | 7/1997 | Kieturakis | |
| 5,646,146 A | 7/1997 | Faarup et al. | |
| 5,649,547 A | 7/1997 | Ritchart et al. | |
| 5,665,085 A | 9/1997 | Nardella | |
| 5,674,184 A | 10/1997 | Hassler, Jr. | |
| 5,676,925 A | 10/1997 | Klaveness et al. | |
| 5,683,384 A | 11/1997 | Gough et al. | |
| 5,687,739 A | 11/1997 | McPherson et al. | |
| 5,688,490 A | 11/1997 | Tournier et al. | |
| 5,715,825 A | 2/1998 | Crowley | |
| 5,720,763 A | 2/1998 | Tovey | |
| 5,741,225 A | 4/1998 | Lax et al. | |
| 5,769,086 A | 6/1998 | Ritchart et al. | |
| 5,772,660 A | 6/1998 | Young et al. | |
| 5,775,333 A * | 7/1998 | Burbank et al. | 600/567 |
| 5,782,764 A | 7/1998 | Werne | |
| 5,782,775 A | 7/1998 | Milliman et al. | |
| 5,794,626 A | 8/1998 | Kieturakis | |
| 5,797,907 A | 8/1998 | Clement | |
| 5,800,378 A | 9/1998 | Edwards et al. | |
| 5,810,806 A | 9/1998 | Ritchart et al. | |
| 5,853,366 A | 12/1998 | Dowlatshahi | |
| 5,876,340 A | 3/1999 | Tu et al. | |
| 5,902,272 A | 5/1999 | Eggers et al. | |
| 5,925,044 A | 7/1999 | Hofmann et al. | |
| 5,928,164 A | 7/1999 | Burbank et al. | |
| 5,947,964 A | 9/1999 | Eggers et al. | |
| 5,964,716 A | 10/1999 | Gregoire et al. | |
| 5,972,002 A | 10/1999 | Bark et al. | |
| 5,980,469 A | 11/1999 | Burbank et al. | |
| 5,984,919 A | 11/1999 | Hilal et al. | |
| 6,004,269 A | 12/1999 | Crowley et al. | |
| 6,050,955 A | 4/2000 | Bryan et al. | |
| 6,056,700 A | 5/2000 | Burney et al. | |
| 6,063,082 A | 5/2000 | DeVore et al. | |
| 6,120,462 A | 9/2000 | Hibner et al. | |
| 6,142,955 A | 11/2000 | Farascioni et al. | |
| 6,161,034 A | 12/2000 | Burbank et al. | |
| 6,234,177 B1 | 5/2001 | Barsch | |
| 6,387,056 B1 * | 5/2002 | Kieturakis | 600/565 |
| 6,454,727 B1 | 9/2002 | Burbank et al. | |
| 6,494,881 B1 | 12/2002 | Bales et al. | |
| 6,540,695 B1 | 4/2003 | Burbank et al. | |
| 6,712,775 B2 | 3/2004 | Burbank et al. | |
| 2001/0002250 A1 | 5/2001 | Burbank et al. | |
| 2003/0004407 A1 | 1/2003 | Carroll et al. | |

FOREIGN PATENT DOCUMENTS

| | | |
|---|---|---|
| DE | 19528440 A1 | 8/1994 |

| | | |
|---|---|---|
| EP | 146699 | 9/1984 |
| EP | 0255123 | 2/1988 |
| EP | 0292936 | 11/1988 |
| EP | 0472368 A2 | 8/1991 |
| EP | 0481685 A1 | 10/1991 |
| EP | 0667126 A1 | 8/1995 |
| EP | 0 919 190 A | 6/1999 |
| EP | 0 919 192 | 6/1999 |
| EP | 0 983 749 | 3/2000 |
| EP | 0 970 658 | 1/2001 |
| GB | 2311468 A | 2/1997 |
| WO | 93/14712 | 5/1993 |
| WO | 93/13718 | 7/1993 |
| WO | PCT/GB94/01536 | 7/1994 |
| WO | 98/06346 | 2/1998 |
| WO | 98/08441 | 3/1998 |
| WO | WO 98/43531 | 10/1998 |
| WO | 99/30764 | 6/1999 |
| WO | 99/44506 | 9/1999 |
| WO | 00/16697 | 3/2000 |
| WO | WO 02/22023 | 3/2002 |
| WO | WO 02/22023 A1 | 3/2002 |
| WO | WO 2005/063126 | 7/2005 |

OTHER PUBLICATIONS

Blackwell Science Ltd., "The Loop Electrode: New Device for US-Guided Interstitial Tissue Ablation Using Radio Frequency Electrosurgery—An Animal Study" 1996 *Min Incas Ther & Allied Technol* 5: 511-516.

F. Burbank, M.D., "Sterotactic Breast Biopsy: Its History, Its Present, and Its Future", *The American Surgeon*, Feb. 1996, vol. 62, pp. 128-150.

Fucci, V., et al., "Large Bowel Transit Times Using Radioopaque Markers in Normal Cats", *J. of Am. Animal Hospital Assn.*, Nov.-Dec. 1995 31 (6) 473-477.

Timothy J. Micklos, "Percutaneous Biopsy Techniques", *Manual of Oncologic Therapeutics*, (1989/1990), pp. 39-42.

Schindlbeck, N.E., et al., "Measurement of Colon Transit Time", *J. of Gastroenterology*, No. 28, pp. 399-404, 1990.

Whitman et al., "Coaxial Core Needle Biopsy Under Mammographic Guidance: Indications and Applications", AJR:171, Jul. 1998, pp. 67-70.

International Search Report for PCT, US 99/21416 mailed May 19, 2000.

Written Opinion mailed Jul. 18, 2000, PCT Rule 66, for International Application PCT/US/9921416.

International Search Report, PCT/US01/43360.

* cited by examiner

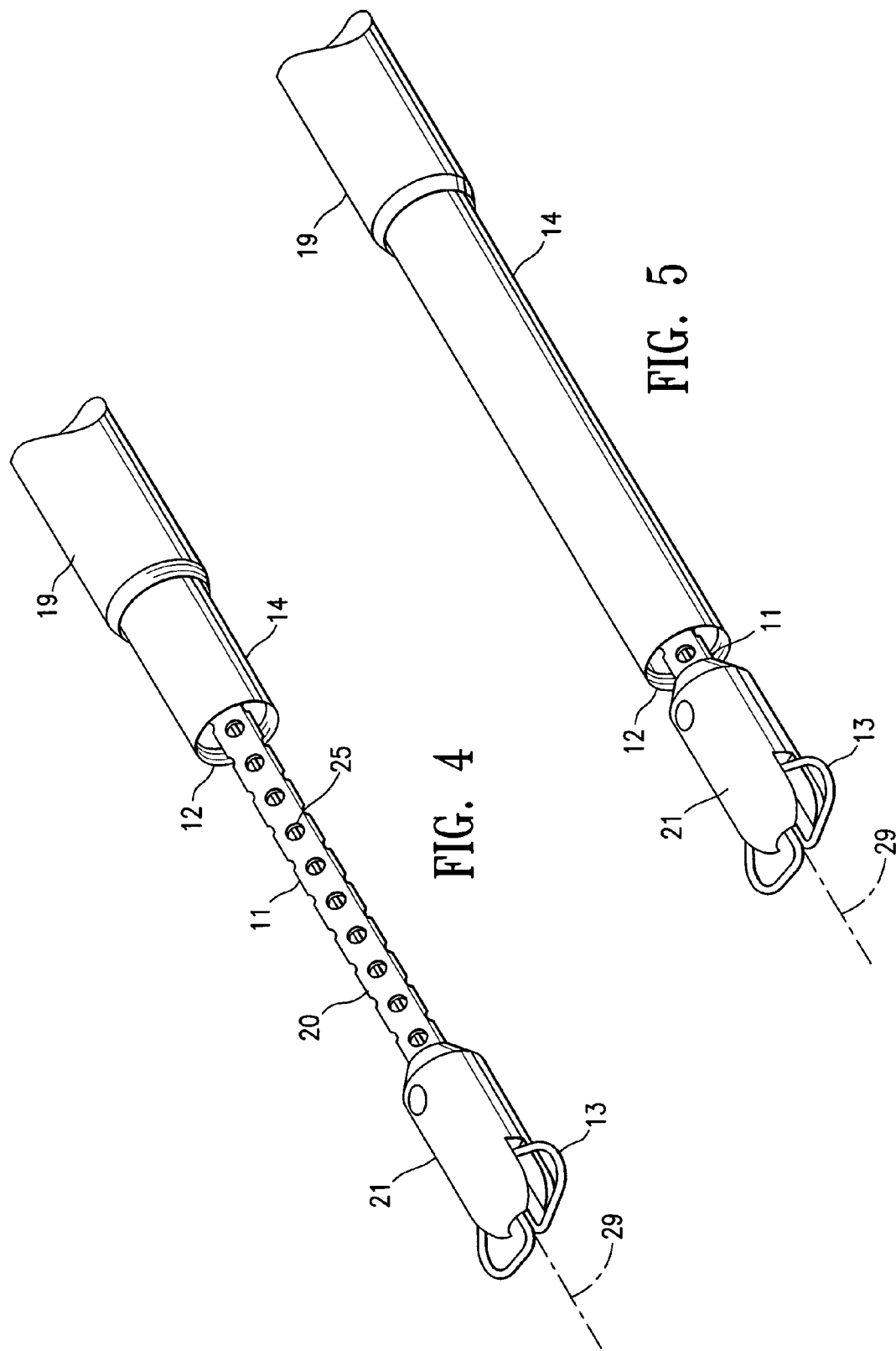

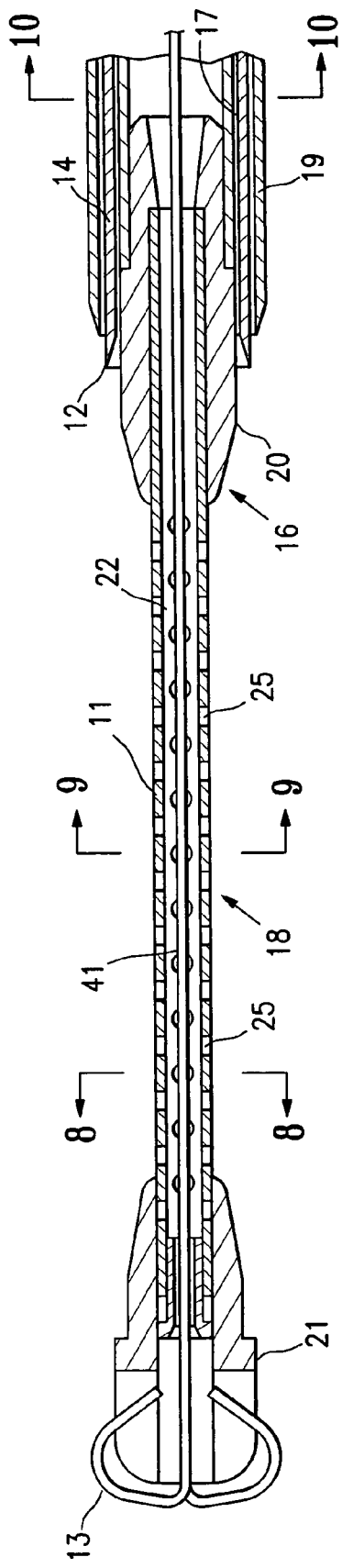
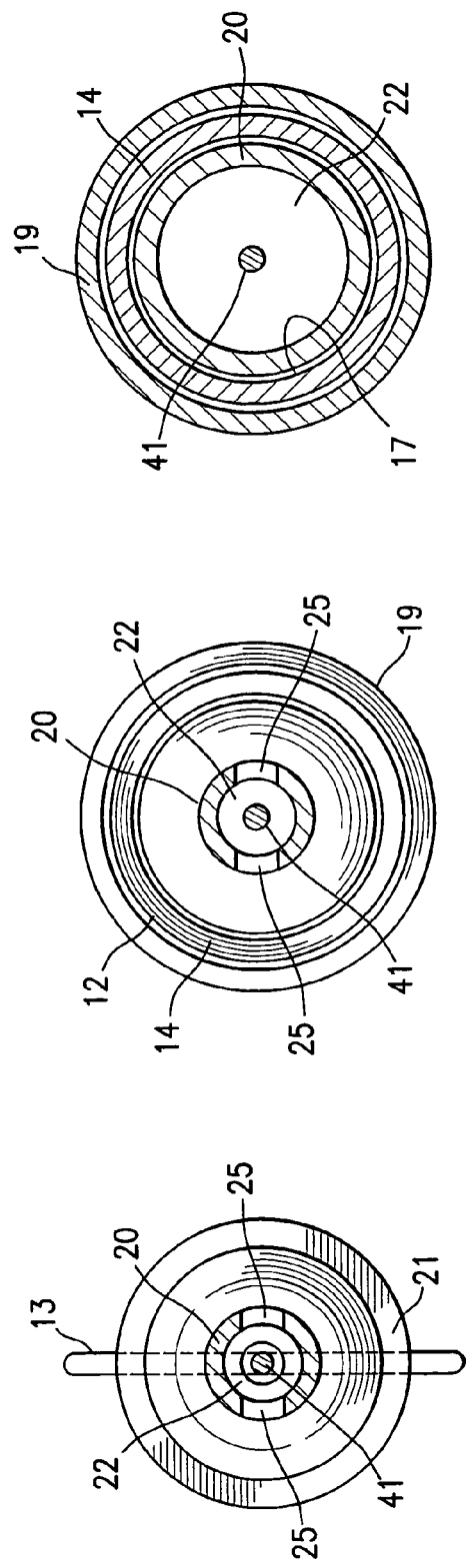
FIG. 7
FIG. 8
FIG. 9
FIG. 10

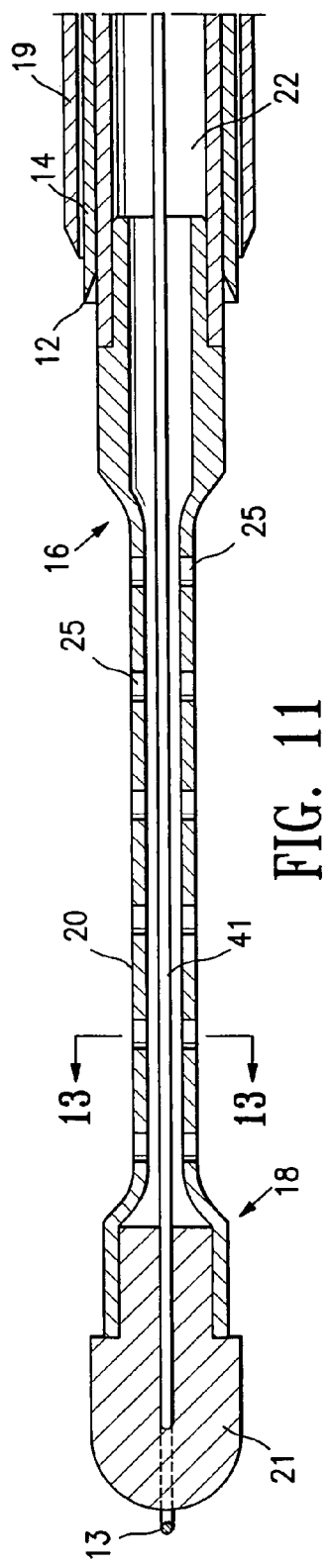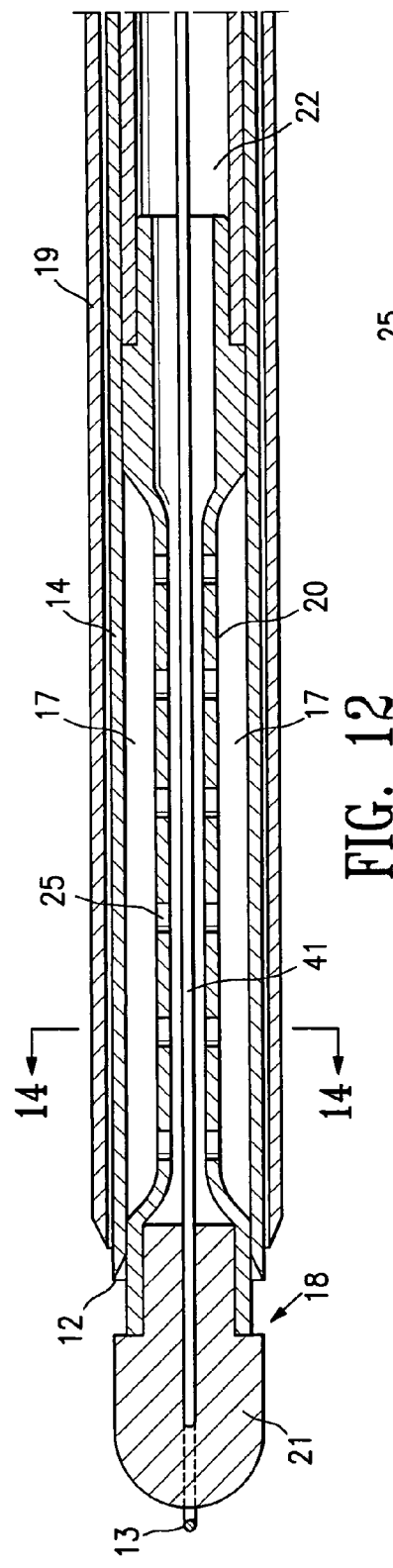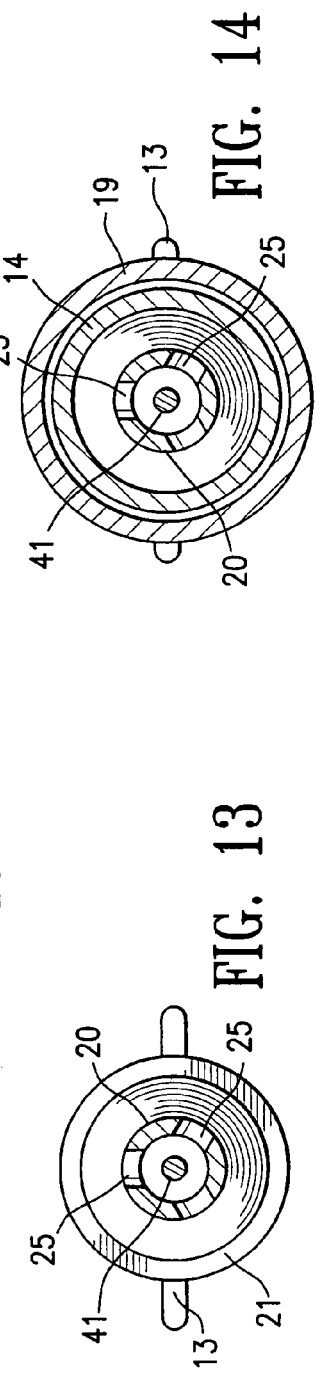

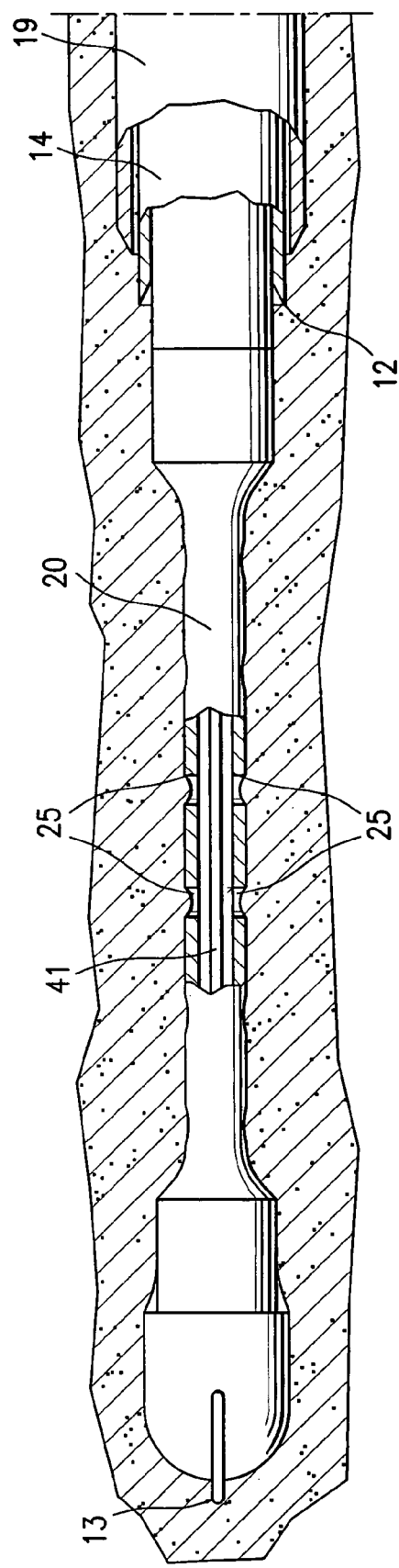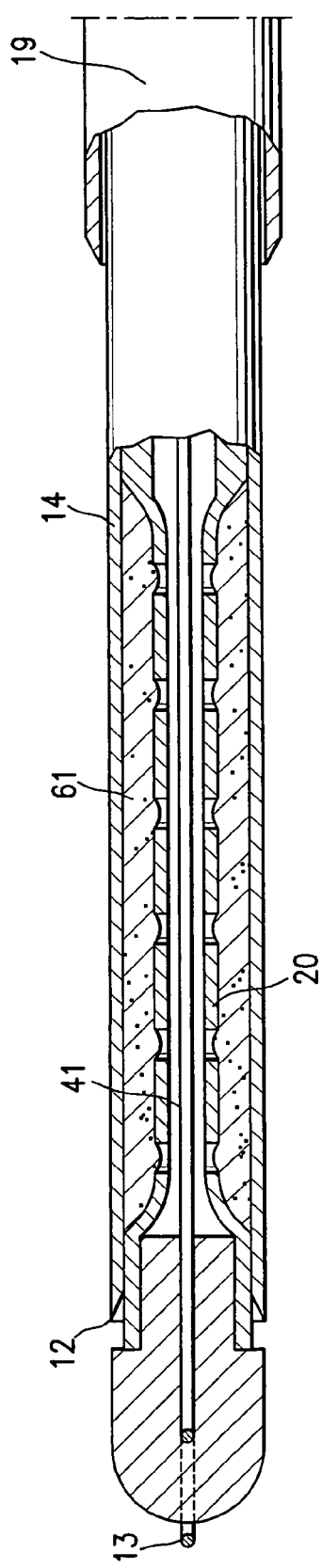

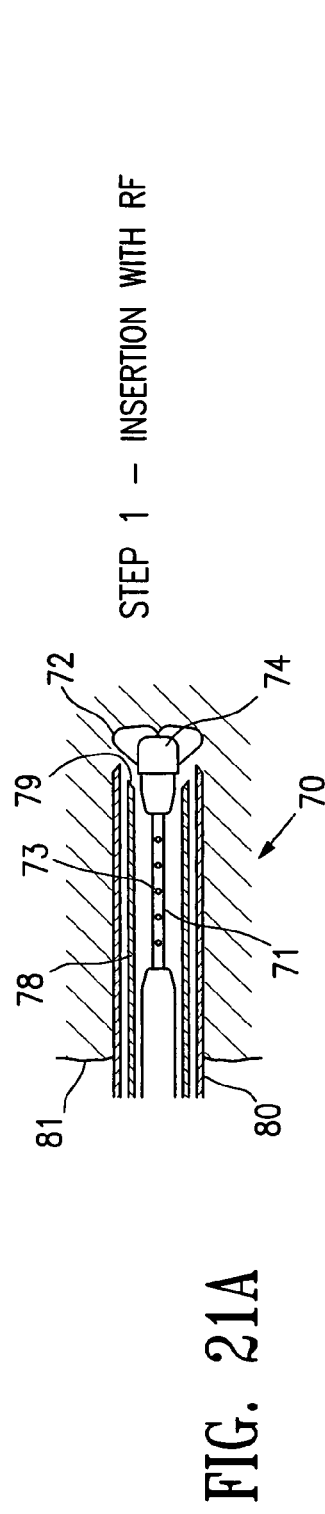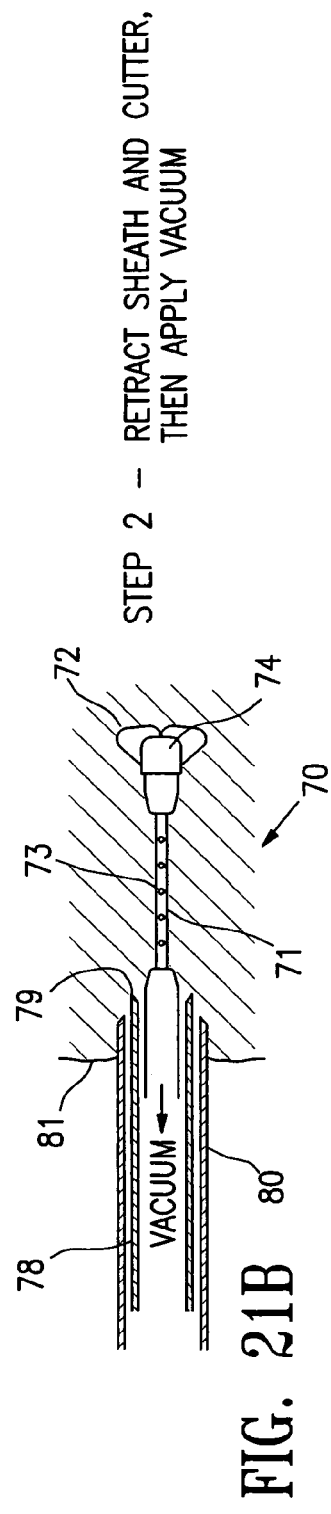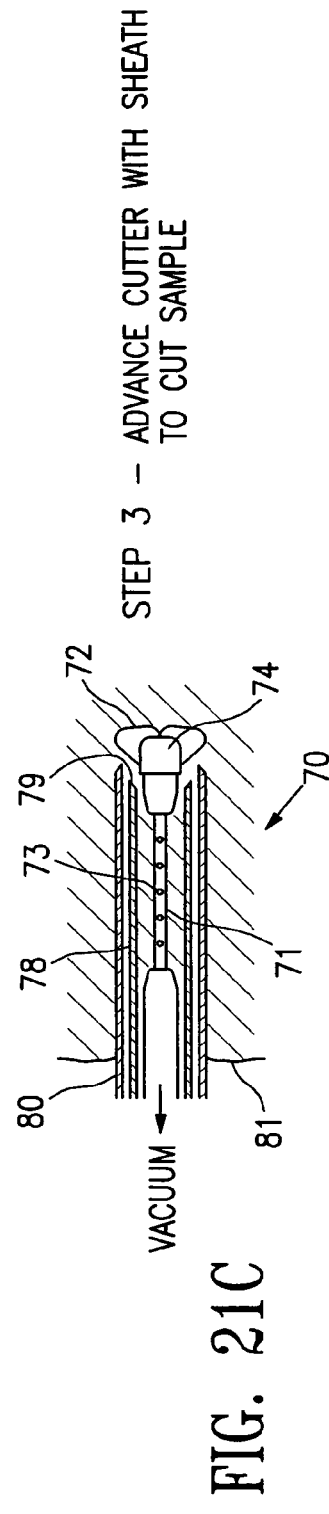
FIG. 21A — STEP 1 – INSERTION WITH RF
FIG. 21B — STEP 2 – RETRACT SHEATH AND CUTTER, THEN APPLY VACUUM
FIG. 21C — STEP 3 – ADVANCE CUTTER WITH SHEATH TO CUT SAMPLE

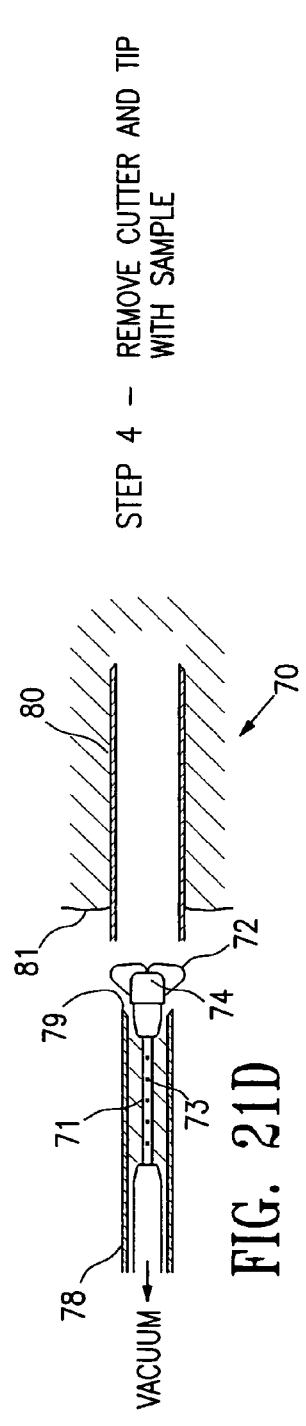
FIG. 21D  STEP 4 – REMOVE CUTTER AND TIP WITH SAMPLE
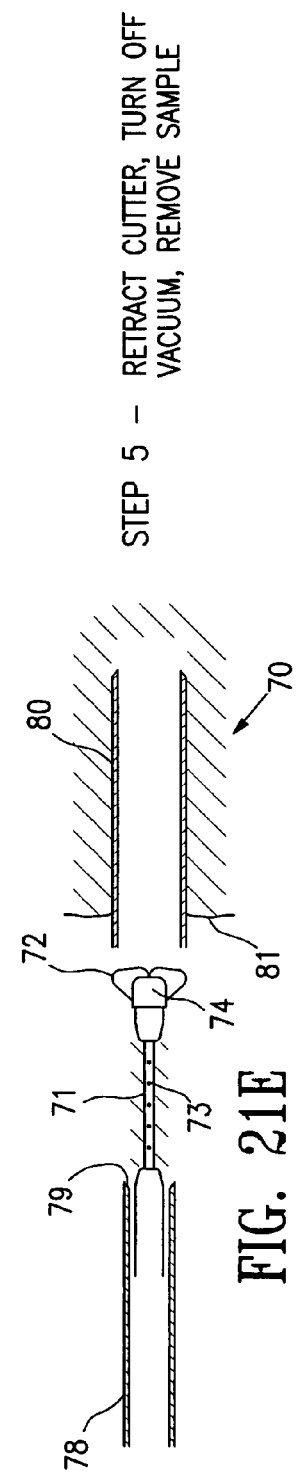
FIG. 21E  STEP 5 – RETRACT CUTTER, TURN OFF VACUUM, REMOVE SAMPLE
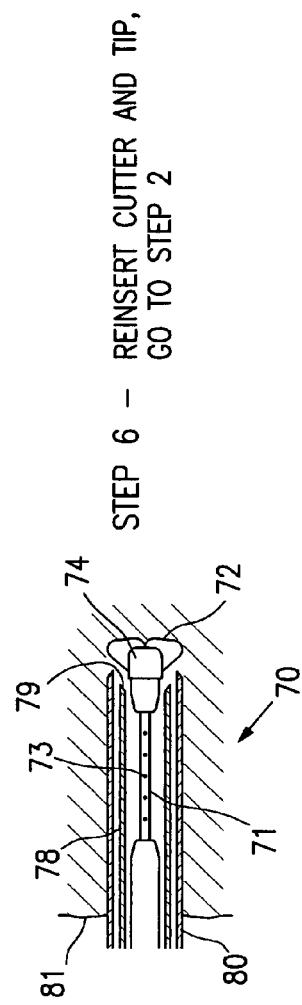
FIG. 21F  STEP 6 – REINSERT CUTTER AND TIP, GO TO STEP 2

APPARATUS AND METHOD FOR ACCESSING A BODY SITE

CROSS-REFERENCE TO RELATED APPLICATIONS

This application is a continuation of patent application Ser. No. 10/179,933, filed on Jun. 21, 2002 (now U.S. Pat. No. 6,758,848) which is a continuation-In-part of patent application Ser. No. 09/717,176, filed Nov. 16, 2000 (now U.S. Pat. No. 6,497,706), all of which applications and patents are hereby incorporated herein by reference in their entirety and from which priority is hereby claimed under 35 U.S.C.§§119(e) and 120.

FIELD OF THE INVENTION

The present invention relates generally to the field of biopsy devices and the methods of using such devices. More specifically, it relates to a device and method for accessing a targeted site of pathologically suspect tissue mass within a patient's body, so as to facilitate the taking of a specimen of the tissue mass.

BACKGROUND OF THE INVENTION

In diagnosing and treating certain medical conditions, such as potentially cancerous tumors, it is usually desirable to perform a biopsy, in which a specimen of the suspicious tissue is removed for pathological examination and analysis. In many instances, the suspicious tissue is located in a subcutaneous site, such as inside a human breast. To minimize surgical intrusion into the patient's body, it is desirable to be able to insert a small instrument into the patient's body to access the targeted site and then extract the biopsy specimen therefrom.

After removing the tissue specimens, additional procedures may be performed at the biopsy site. For example, it may be necessary to cauterize or otherwise treat the cavity which results from tissue specimen removal to stop bleeding and reduce the risk of infection or other complications. Also, it may be advantageous to mark the site for future surgical procedures should pathological tests performed on the biopsy specimen indicate surgical removal or other treatment of the suspected tissue mass from which the specimen was removed. Such marking can be performed, for example, by the apparatus and method disclosed and claimed in co-pending U.S. patent application Ser. No. 09/343,975,filed Jun. 30, 1999, entitled "Biopsy Site Marker and Process and Apparatus for Applying It," which is hereby incorporated by reference in its entirety.

Electrosurgical techniques have been used in a variety of circumstances, including certain types of biopsy procedures. In electrosurgery, high frequency electrical energy is applied through an active electrode to patient tissue. The electrical energy flows through the tissue from the active electrode to a return electrode which is in contact with the patent's tissue and which may be on the exterior of the patient's body or intracorporeally disposed. Typically, the return electrode is attached to the patient at a point remote from where the primary or active electrode contacts the tissue. The tissue adjacent the primary electrode is ablated, to form an opening in the tissue. An electrosurgical biopsy instrument is disclosed and claimed in U.S. patent application Ser. No. 09/159,467 for "Electrosurgical Biopsy Device and Method," assigned to the assignee of the subject application, and which is hereby incorporated by reference in its entirety.

SUMMARY OF THE INVENTION

This invention is directed to a biopsy device that provides ready access to a targeted tissue site within a patient's body and provides for the separation and capture of a tissue specimen from the target tissue site. The biopsy device of the invention generally includes an elongated probe having a proximal end and a distal end and an inner lumen extending therein which is configured to be in fluid communication with a vacuum source. A small-dimensioned distal probe section is provided which has transverse dimensions less than adjacent probe portions distal to the small-dimensioned section, and which has one and preferably a plurality of apertures in a wall thereof in fluid communication with the probe's inner lumen. A circular cutter is slidably disposed about the probe member and configured for rotation around, and translation along, the probe. Such longitudinal translation may be for a partial length, and preferably is for the entire length of the small-dimensioned distal probe section. The cutting surface of the circular cutter is disposed in a plane which is generally transverse and preferably perpendicular to the longitudinal axis of the probe.

The proximal end of the probe is configured to allow the inner lumen of the probe to be connected to a vacuum source, so that when a vacuum is applied to the inner lumen, tissue adjacent to the small-dimensioned distal probe section is pulled into contact with the distal probe section and thereby secures the tissue specimen to the distal probe section. With the tissue specimen secured to the distal probe section, the circular cutter may then be advanced distally, and preferably also rotated, to thereby separate the tissue specimen from the surrounding tissue bed to which the tissue specimen is secured and supported. The probe and the tissue specimen secured thereto may then be withdrawn from the patient.

In a preferred embodiment of the invention, the biopsy device has a thin, arcuate shaped distal electrode connected to the distal end of the probe and spaced distally therefrom as disclosed in copending application Ser. No. 09/477,255, filed on Jan. 4, 2000, and as disclosed in U.S. Pat. No. 6,331,166, both of which are incorporated by reference above. The distal arcuate electrode preferably lies in a plane that is parallel to and generally passes through a longitudinal axis of the elongated probe. The distal arcuate electrode preferably includes two or more electrode portions configured to flex or move in radial directions, such as within the plane parallel to the longitudinal axis. The maximal chordal dimension of the distal electrode is typically at least as large as the diameter of the distal end of the elongated probe, and is preferably greater than the diameter of the distal end of the probe to ensure that an opening made by the electrode is large enough to allow the biopsy device to be readily advanced through the tissue to the target site and through the suspicious tissue that will form at least part of the tissue specimen. Moreover, the distal electrode makes a planar cut through the desired specimen as it advances through tissue. Thus, when the circular cutter severs a specimen from supporting tissue as it advances over the small-dimensioned distal probe section, the specimen is typically formed circumferentially around the small-dimensioned distal probe section. Where the specimen includes the planar cut made by the distal electrode, the specimen may be split into two or more sections.

In a presently preferred embodiment, the biopsy device is provided with an access cannula, within which is disposed a supporting tube that is slidably disposed around and along a length of the probe. The supporting tube is disposed so as to cover at least part of the small-dimensioned distal probe section during advancement through tissue. The circular cutter is preferably disposed on the distal end of the supporting tube, and is configured to rotate within and to move longitudinally within the access cannula; the circular cutter is also configured to extend beyond the distal end of the access cannula, as it advances distally around the small-dimensioned distal probe. The access cannula may retract and advance as necessary to expose or cover portions of the circular cutter and supporting tube. In distal configurations, the access cannula, circular cutter and supporting tube may cover at least part of and preferably all of the small-dimensioned probe. When the access cannula, circular cutter and supporting tube are disposed in proximal configurations, at least a portion of the small-dimensioned probe may be exposed and configured to allow specimen tissue to be brought into contact with the small-dimensioned distal probe section. A vacuum may be applied to the inner lumen of the probe effective to pull tissue towards the small-dimensioned probe and to pull tissue into contact with the small-dimensioned probe where the specimen is secured. The circular cutter may be a separate member secured to or formed by the distal end of the supporting tube. Longitudinal translation of the circular cutter and supporting tube, preferably with rotation, is effective to separate a tissue specimen, or specimens, from the adjacent tissue. The supporting tube, with the circular cutter attached at its distal end, translates longitudinally at least partially within the access cannula, which serves to support and guide the supporting tube and cutter. The circular cutter and a distal portion of the supporting tube may extend distally from a distal end of the access cannula during distal translation and preferably rotation of the circular cutter. The access cannula also serves to shield and to protect body tissue from contact with a portion of the supporting tube as it translates and preferably also rotates during cutting operation.

Distal translation of the supporting tube over the small-dimensioned distal probe section effectively encloses and captures the severed tissue specimen(s) within the interior of the supporting tube.

After acquisition of a tissue sample, the biopsy device may be withdrawn from the patient, and once withdrawn, the specimen or specimen sections may be removed from the distal probe section for subsequent pathological examination. Alternatively, the probe, including the small-dimensioned distal probe section and the cutter attached to the supporting tube may be withdrawn, and samples recovered, while the access cannula remains in position at least partially within a patient's body. The retention of the access cannula in place at least partially within a patient's body aids in the recovery of subsequent samples, and aids in the delivery of markers, drugs, and the like to the location from which a tissue specimen was obtained.

The distal electrode is connected by means of an electrical conductor which extends to the proximal extremity of the probe, preferably through the inner lumen of the probe to a source of high frequency, e.g. radiofrequency (RF), electrical power.

The probe, including the distal radiofrequency cutter, proximal circular cutter and the supporting tube, and optionally the access cannula, are preferably configured for hand operation, or may be powered by a hand unit connected to a suitable controller. The probe, or components of the probe, including such components as the circular cutter and its attached supporting tube, the access cannula, and other components, are preferably configured to be sterilizable and to be disposable.

These and other advantages of the invention will become more apparent from the following detailed description of the invention and the accompanying exemplary drawings.

BRIEF DESCRIPTION OF THE DRAWINGS

FIG. 4 is an enlarged perspective view of the distal section of the biopsy device shown in FIG. 2 with the supporting tube in an opened configuration.

FIG. 5 is an enlarged perspective view of the distal section of the biopsy device shown in FIG. 2 with the supporting tube in a closed configuration.

FIG. 7 is an enlarged longitudinal cross-sectional view of the distal section of the device shown in FIG. 6.

FIG. 8 is a transverse cross sectional view of the device shown in FIG. 7 taken along the lines 8—8.

FIG. 9 is a transverse cross sectional view of the device shown in FIG. 7 taken along the lines 9—9.

FIG. 10 is a transverse cross sectional view of the device shown in FIG. 7 taken along the lines 10—10.

FIG. 11 is an enlarged longitudinal cross-sectional view of the distal section of the device shown in FIG. 6 rotated 90° from the view shown in FIG. 7.

FIG. 12 is an enlarged longitudinal cross-sectional view of the distal section of the device as shown in FIG. 11 with the supporting tube in a closed configuration.

FIG. 13 is a transverse cross sectional view of the device shown in FIG. 11 taken along the lines 13—13.

FIG. 14 is a transverse cross sectional view of the device shown in FIG. 12 taken along the lines 14—14.

FIG. 16 is a transverse cross sectional view of the device shown in FIG. 12 disposed within a tissue site and tissue at the site held against the surface of the distal extremity by the action of a vacuum within the inner lumen of the probe.

FIG. 17 is a transverse cross sectional view of the device shown in FIG. 15 with the supporting tube in a closed configuration with a separated tissue specimen within the space between the distal extremity 20 and the interior of the supporting tube 14.

FIG. 21A is a longitudinal cross-sectional view of a device embodying features of the invention as in FIG. 20, shown configured for insertion into a patient's body.

FIG. 21B is a longitudinal cross-sectional view of a device embodying features of the invention as in FIG. 21A, shown configured with the access cannula and supporting tube retracted.

FIG. 21C is a longitudinal cross-sectional view of a device embodying features of the invention as in FIG. 21A, shown after advancement of the supporting tube and access cannula and cutting of a tissue sample.

FIG. 21D is a longitudinal cross-sectional view of a device embodying features of the invention as in FIG. 21A, showing portions of the device removed from within the access cannula which remains in place in body tissue.

FIG. 21E is a longitudinal cross-sectional view of a device embodying features of the invention as in FIG. 21A, shown configured for removal of a tissue sample from the device.

FIG. 21F is a longitudinal cross-sectional view of a device embodying features of the invention as in FIG. 21A, shown after re-insertion into a patient's body and configured for recovery of another tissue sample.

DETAILED DESCRIPTION OF THE INVENTION

Figure 1:
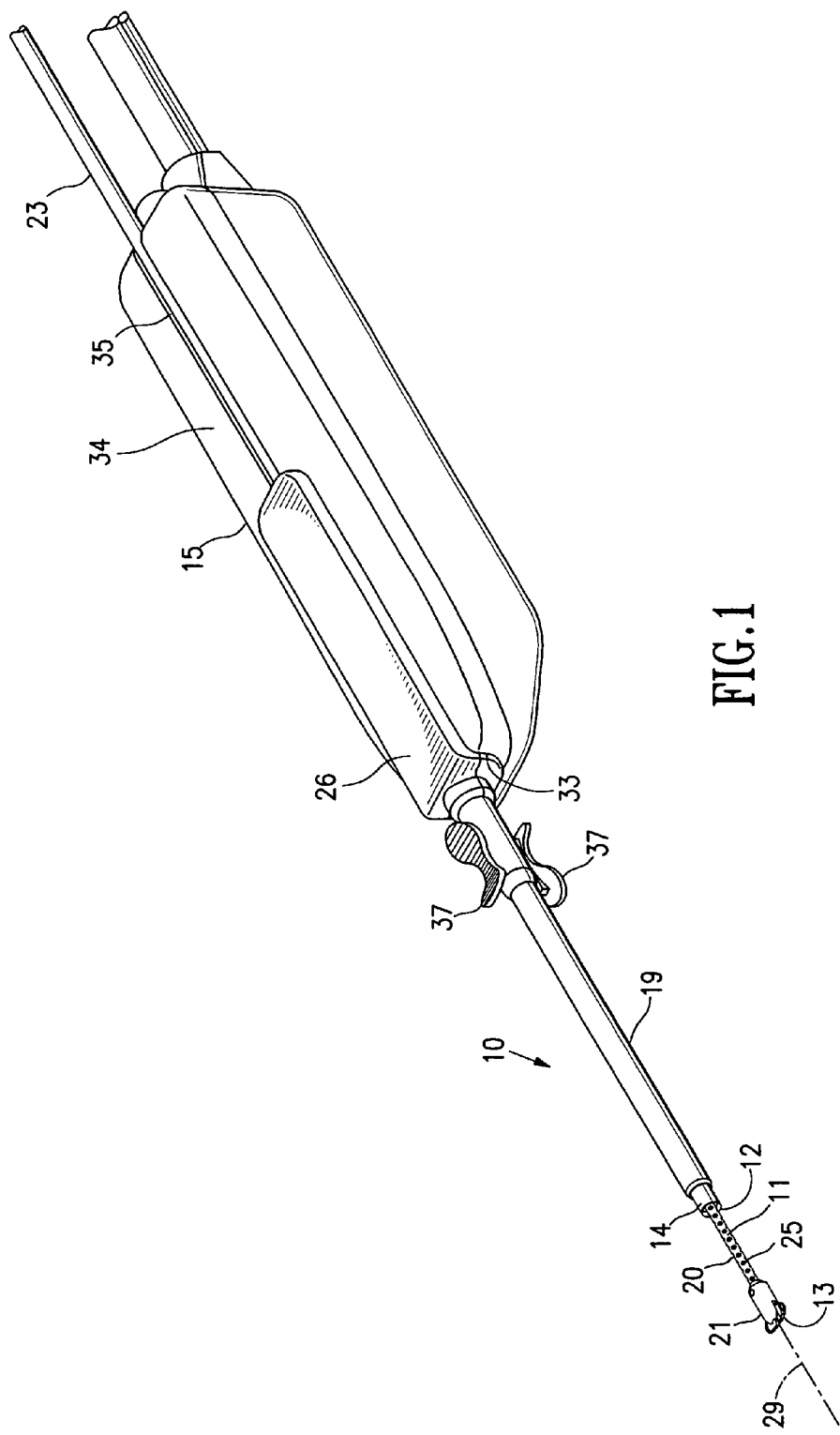
FIG. 1 is a perspective view of a removable biopsy device having features of the invention seated within a handle with the supporting tube of the device in an opened configuration.
Figure 2:
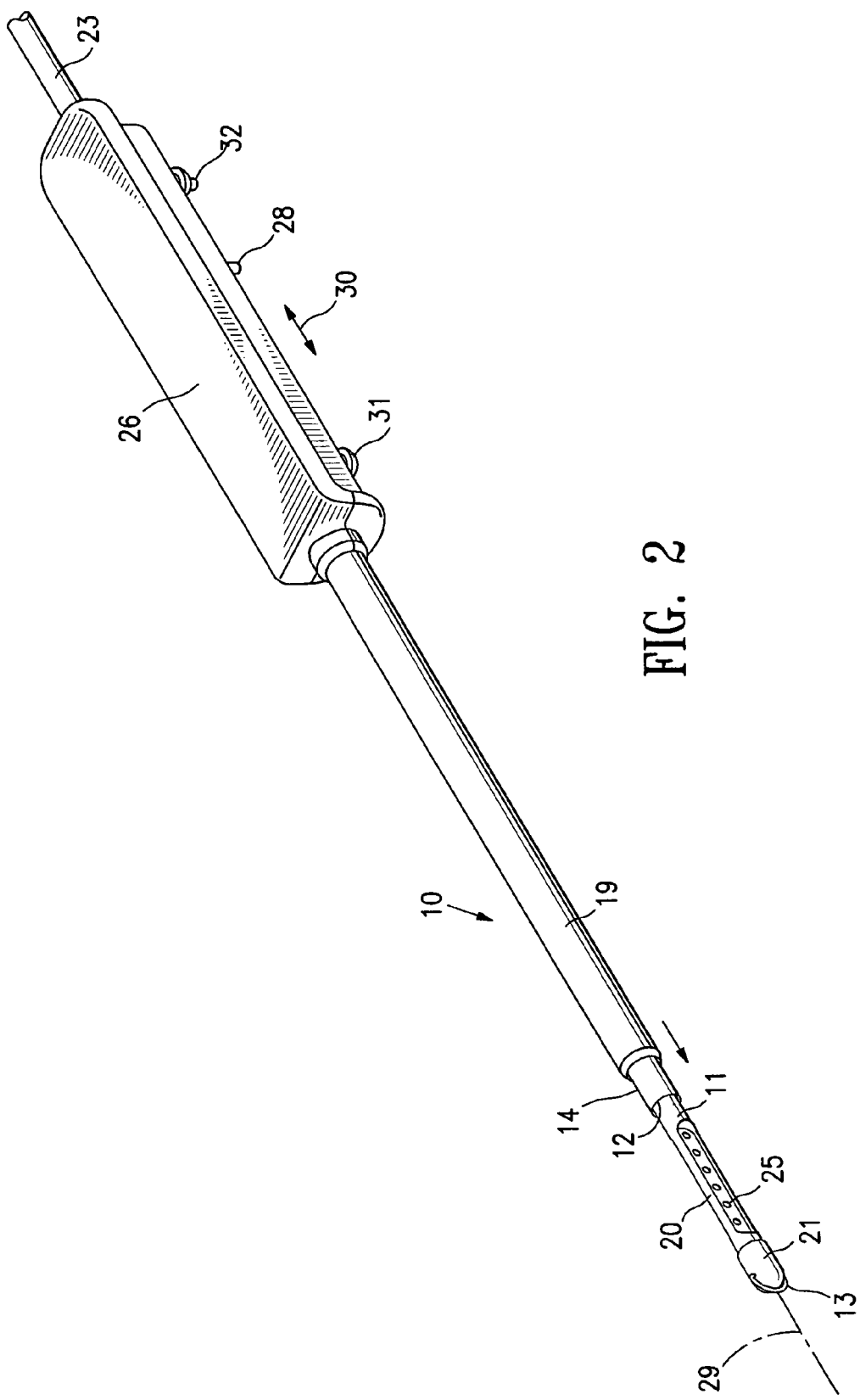
FIG. 2 is a perspective view of the biopsy device shown in FIG. 1 removed from the handle.

Reference is made to FIGS. 1–14 which illustrate a biopsy device 10 embodying features of the invention. The device 10 generally includes an elongated probe member 11, a tissue-cutting blade 12, a tissue-cutting electrode 13 and a supporting tube 14 carrying tissue-cutting blade 12. The tissue-cutting electrode 13 preferably includes at least two components, as illustrated in FIG. 1, although it may be a single wire electrode, as illustrated in FIG. 2. The supporting tube 14 is slidably disposed about the probe 11 and is slidably disposed within access cannula 19. In one embodiment of the invention shown in FIG. 1, the device 10 is a disposable device and is configured to be mounted on a handle 15 which is configured to provide mechanical and electrical power, vacuum, and control to the device. For example, a handle 15 may be configured to provide mechanical power effective to power the longitudinal translation, rotation, reciprocation, or other movement of tissue-cutting blade 12, supporting tube 14, or other movable element of device 10. Alternatively, mechanical and/or electrical power may be provided by housing 26, or by handle 15 and housing 26. As illustrated in the FIGS. 1, 3, and 6, handle 26 may include finger holders 37 configured to receive a finger or thumb of an operator. Finger holders 37 are configured to release housing 26 from handle 15 when they are squeezed by an operator.

The probe member 11 has a proximal section 16 and a distal section 18. Proximal section 16 is configured for slidable disposition within the inner lumen 17 of the supporting tube 14. Proximal section 16 acts to guide supporting tube 14 and to protect tissue-cutting blade 12 as the supporting tube 14 and cutter 12 translate and rotate around probe 11 and within access cannula 19. Distal section 18 includes a distal extremity 20 which is configured to secure tissue from a tissue site which is to form the specimen and an enlarged distal end 21 to which the tissue-cutting electrode 13 is secured. The probe member 11 may be cylindrical, with a circular cross-section, or may have a square, rectangular, or other shaped cross-section.

As shown in FIGS. 4 and 5, tissue-cutting blade 12 and supporting tube 14 are configured to translate longitudinally so as to expose distal extremity 20 when in a proximal configuration, and to cover distal extremity 20 when in a distal configuration. Distal extremity 20 may be partially covered when tissue-cutting blade 12 and supporting tube 14 are in configurations intermediate to those illustrated in FIGS. 4 and 5, and may be more completely covered or exposed when tissue-cutting blade 12 and supporting tube 14 are in configurations more distal or proximal to those illustrated in FIGS. 4 and 5. During such longitudinal translation, tissue-cutting blade 12 may rotate (in one or more rotational directions) and/or may reciprocate longitudinally. In preferred embodiments, tissue-cutting blade 12 remains separated by a gap 38 from enlarged distal end 21 of probe 11 at its most distal position (e.g., FIG. 20).

Figure 6:
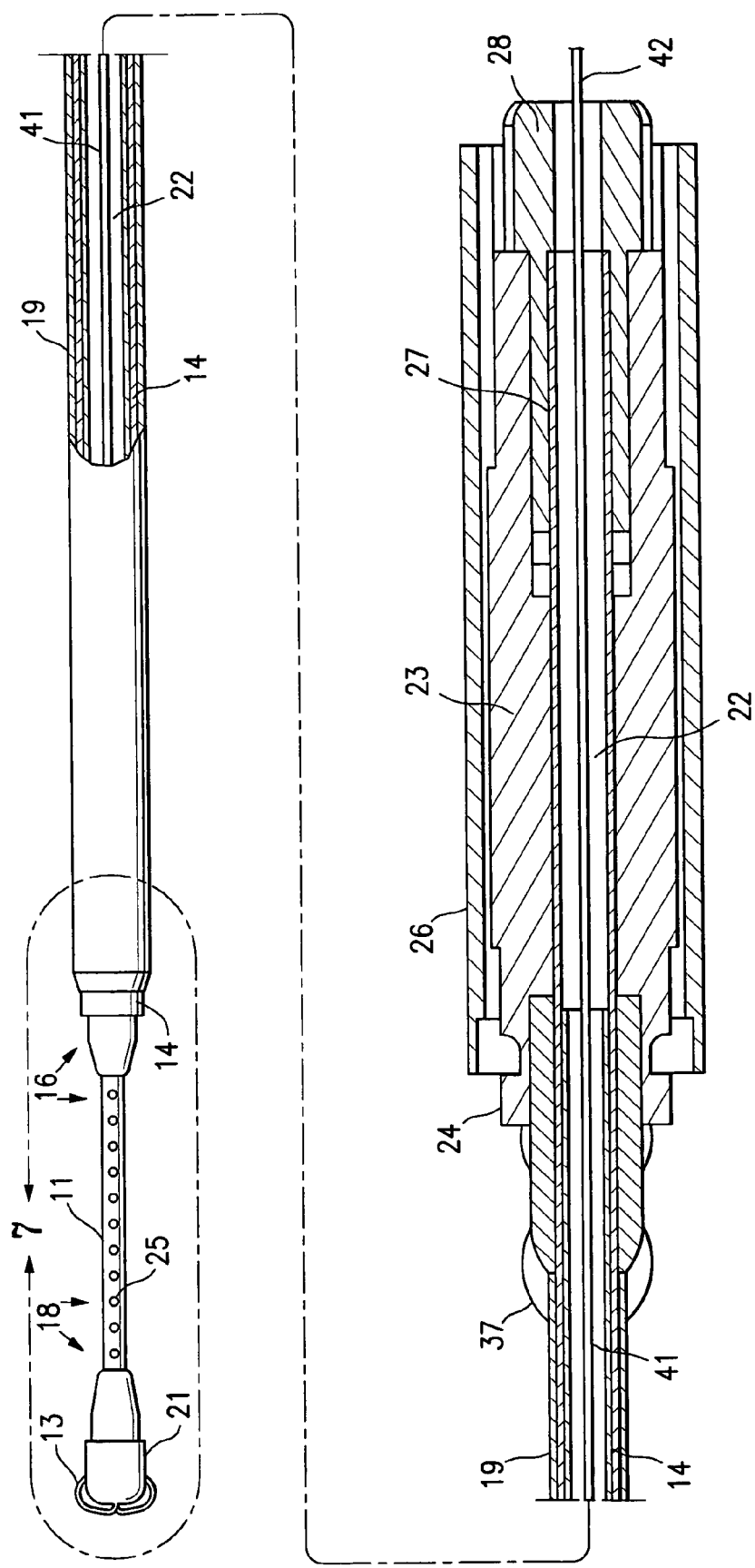
FIG. 6 is a longitudinal cross-sectional view of the device shown in FIG. 3 taken along the lines 6—6.

As shown in more detail in FIGS. 6–10, the probe member 11 is provided with an inner lumen 22 which extends from the distal extremity 20 to a connection member 23 on the proximal end 24 of the probe member 11 and which is in fluid communication with the plurality of aspiration ports 25 provided on the distal extremity 20 of the probe member 11. The proximal end 24 of the probe member 11 and the connection member 23 are secured within the housing 26 as shown in FIG. 6.

The supporting tube 14 is slidably disposed about the proximal section of the probe member 11 and has a proximal end secured to a slidable collar 27 within the housing 26. The collar 27 is provided with an connector 28 (which may be an arm as in FIG. 2 or a gear as in FIG. 3) which is configured to seat within a receiving opening on a driver (not shown) provided in the handle 15. The collar 27 is configured to be slidably disposed within the housing so that the driver on the handle can move the arm 28 and as a result translate the outer tubular sheath as shown by the arrow 30 in FIG. 2 between an opened and closed configuration. Supporting tube 14 is also configured to rotate around a longitudinal axis 29 as well as to translate longitudinally within access cannula 19. Translation of the supporting tube 14 and tissue-cutting blade 12 may include reciprocation (i.e., alternated distal and proximal translation) as well as rotation, as the supporting tube 14 and tissue-cutting blade 12 move generally in a longitudinal direction.

As illustrated in FIG. 2, a housing 26 may be provided with distal projection 31 and proximal projection 32 which are designed to tightly seat within receiving openings (not shown) provided in the handle 15 to effect a snap fit of the housing 26 within a recess 33 provided in the upper surface 34 of handle 15 as shown in FIG. 1. A second long recess 35 is provided in the upper surface 34 of handle 15 which is contiguous with recess 33 and which is configured to receive the connection member 23 tightly enough to prevent accidental excursions out of the recess. Connection member 23 has an inner lumen in fluid communication with the inner lumen 22 of the probe member 11. Distal projection 31 may be connected to collar 27 attached to supporting tube 14 so that longitudinal translation of proximal projection 32 towards distal projection 31 causes accessing cannula 19 and supporting tube 14 to move distally. In preferred embodiments, accessing cannula 19 and supporting tube 14 move longitudinally in concert, with supporting tube 14 free to rotate within accessing cannula 19.

Figure 3:
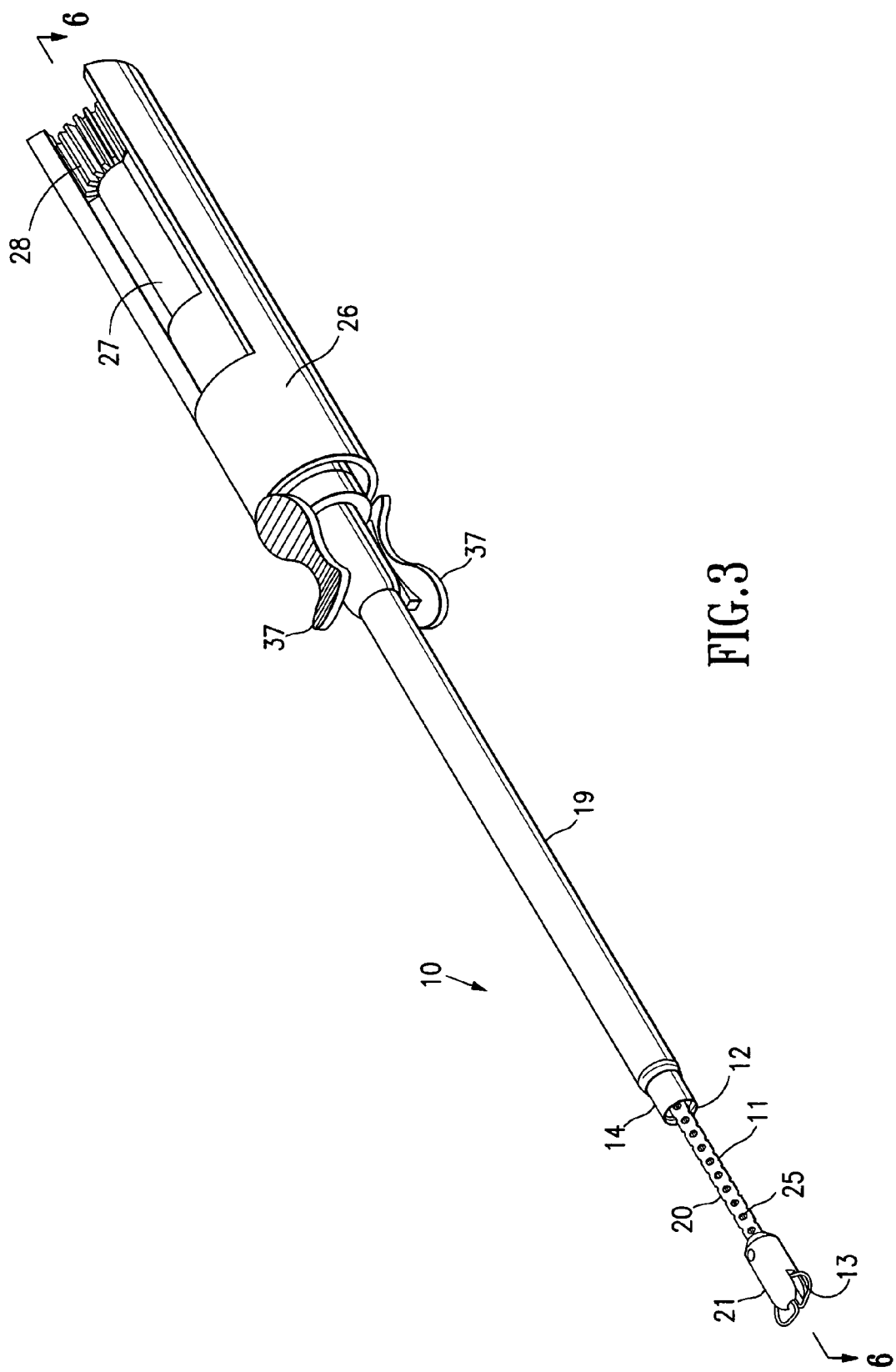
FIG. 3 is a perspective view of the biopsy device shown in FIG. 2 rotated 180° about its longitudinal axis.

The tissue-cutting blade 12, which is circular and disposed about the probe member 11, has a sharp edge that is preferably beveled to have a sharp edge on the outer diameter of the circular blade, although a blade with a leading edge on the inner diameter of a tube is also suitable. The tissue-cutting blade 12 is connected to and supported by the wall of supporting tube 14. This construction allows the tissue-cutting blade 12 to travel longitudinally with the supporting tube 14 within access cannula 19 over the distal extremity 20 of the probe member 11, and thus to extend out of access cannula 19. In this configuration, with the tissue-cutting blade 12 disposed distally to the end of the access cannula 19, the tissue-cutting blade 12 is effective to cut a tissue specimen from tissue held against the distal extremity 20 by the action of a vacuum within the inner lumen 22 from the tissue site, and at the same time to cover the separated tissue specimen with the supporting tube 14. The inner surface of supporting tube 14 may be coated (e.g., with teflon) to reduce friction. In preferred embodiments, the inner diameter of the supporting tube 14 proximal to the tissue cutting blade 12 is greater than the inner diameter of the supporting tube 14 at the region of contact between the tissue-cutting blade 12 and the supporting tube 14, providing greater volume for a tissue sample. Thus, the specimen can be removed with device 10 from the patient with the same, or nearly the same, movement that severs the specimen from surrounding tissue. As shown in FIG. 3, the collar 27 and the gear 28 are configured to drive and to translate the supporting tube 14 both rotationally and longitudinally.

The tissue-cutting electrode 13 has an arcuate portion which is spaced distally away from the distal end 21 and has a maximum chord (i.e. distance between the ends of the arcuate portion) which is preferably larger than the maximum diameter of the distal end. The maximum width of the tissue-cutting electrode 13 is preferably about 20 to about 50% greater than the maximum outside transverse dimension of the distal end 21 of the probe 11. The tissue-cutting electrode 13 can be spaced distally from an outer surface of the distal end 21 by a distance of about 0.01 to about 0.05 inch, preferably about 0.02 to about 0.04 inch. As shown in FIGS. 6 and 7, the arcuate tissue-cutting electrode 13 is formed out of the distal extremity of electrical conductor 41. The proximal end 42 of the conductor 41 is electrically connected via a conductor to an electrosurgical generator which can supply high frequency electrical power.

The shaft of the device 10 which extends out from the housing 26 may have a length of about 3 to about 15 cm, preferably, about 5 to about 13 cm, and more specifically, about 8 to about 9 cm for breast biopsy use. To assist in properly locating the shaft of device 10 during advancement thereof into a patient's body, (as described below), the distal extremity 20 of the probe 11, the access cannula 19, and the supporting tube 14 may be provided with markers at desirable locations that provide enhanced visualization by eye, by ultrasound, by X-ray, or other imaging or visualization means. An echogenic polymer coating that increases contrast resolution in ultrasound imaging devices (such as ECHOCOAT™ by STS Biopolymers, of Henrietta, N.Y.) is suitable for ultrasonic visualization. Radiopaque markers may be made with, for example, stainless steel, platinum, gold, iridium, tantalum, tungsten, silver, rhodium, nickel, bismuth, other radiopaque metals, alloys and oxides of these metals. In addition, the surfaces of the device in contact with tissue may be provided with a suitable lubricious coating such as a hydrophilic material or a fluoropolymer.

The proximal portion of the probe 11 generally has an outer dimension of about 3 to about 10 mm and a inside dimension of about 2 to about 6 mm and it may be desirable in some embodiments to have a close fit between the proximal section of the probe 11 and the inner lumen 17 of supporting tube 14 to avoid a gap therebetween which can catch or snag on adjacent tissue during advancement through tissue and impede advancement. Similarly, it may be desirable in some embodiments to have a close fit between the supporting tube 14 and the access cannula 19, in order to avoid a gap therebetween which can catch or snag on adjacent tissue during advancement through tissue and impede advancement.

The tissue-cutting blade 12 is preferably the sharpened edge of a metal supporting tube 14, or a sharpened metal band ringing the distal end of the supporting tube 14, although any sharp blade attached to the supporting tube 14 is suitable. The tissue-cutting blade 12 may be made from any strong, durable material that can hold a sharp edge, for example, a hard biocompatible metal such as stainless steel, titanium, or other metals, alloys, and compounds. A tissue-cutting blade may also be made from ceramic, glass, or other material having suitable strength and ability to maintain a sharp edge.

The tissue-cutting electrode 13 can be formed with generally conductive wire formed of metallic materials such as stainless steel, tungsten, titanium, molybdenum, and other metals and metal alloys, including refractory metals and alloys containing refractory metals. The shaft components from which the probe 11 and supporting tube 14 are formed may be conventional medical grade polymer materials such as, for example, polycarbonate and liquid crystal polymer (LCP), respectively.

In preferred embodiments, the supporting tube 14 is stainless steel. However, metals, ceramics, glasses, and other materials capable of forming a sharp edge are also suitable. For example, a supporting tube 14 may be made with an epoxy-braid material. Although stainless steel and other metals are preferred, an advantage of forming a supporting tube 14 from epoxy-braid materials, or from other non-conductive materials, is that capacitative coupling with electrical components connected to the tissue-cutting electrode 13 is reduced. Where a supporting tube 14 is made from a such non-conductive materials, a metal tissue-cutting blade 12 may be attached to the distal end of the supporting tube 14. Preferably, materials used in the construction of a device 10 are sterilizable, and suitable for use in disposable medical instruments.

Figure 15:
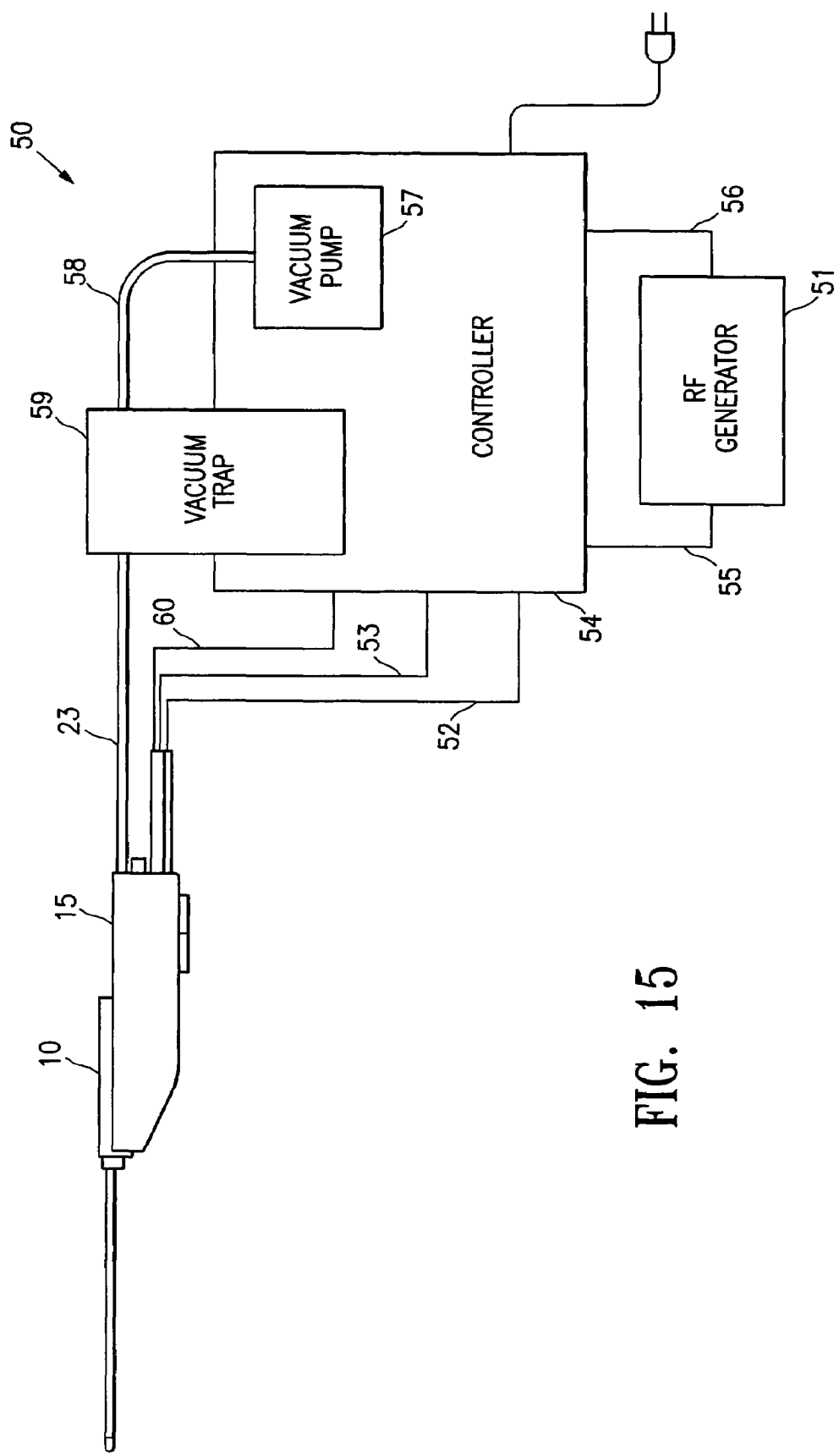
FIG. 15 schematically illustrates an operative system embodying the devices of the invention.

The biopsy device 10 may be used to obtain a tissue specimen utilizing the operation system 50 schematically shown in FIG. 15. The operating system 50 generally includes a high frequency (e.g. RF) electrical power generator 51, which is electrically connected to the tissue-cutting electrode 13 on the biopsy device 10 through conductors 52 and 53. The power output and the receiving element is controlled by the controller 54. The RF generator 51 is electrically connected to the controller through conductors 55 and 56 and preferably operates at about 300 to about 1000 KHz, specifically, about 700 to about 900 KHz and has a power output of about 50 to about 150 watts, preferably, about 80 to about 100 watts. Vacuum is generated by the vacuum pump 57 which is connected in a fluid flow relationship with the inner lumen (not shown) provided in conduit 58 which leads to a vacuum trap 59. Vacuum is applied to the inner lumen 22 of the probe member 11 through inner lumen 36 of connection member 23 connected to the vacuum trap. A meter actuation and control cable 60 is provided to power and control the actuation elements in handle 15.

A patient's skin must be breached in order to gain access to a body site where a tissue specimen is to be obtained. A scalpel or other surgical instrument may be used to make an initial incision in the skin; some physicians may prefer to first make an incision with a scalpel through the patient's skin and expose subcutaneous tissue before passing the device 10 through the tissue. Alternatively, access through the skin may be achieved without such an initial incision by pressing the energized tissue-cutting electrode 13 of the device 10 against an exterior site on the patient's skin proximate to the tissue site where a tissue specimen is to be obtained. High frequency electrical power from the generator 51 passes through the electrical conductor 41 to energize the tissue-cutting electrode 13.

Once the skin is breached by any suitable means, the device 10, with the tissue-cutting electrode 13 energized is advanced through the tissue until the distal end 21 of the device 10 has passed through the tissue which is to form the specimen. The cutting action of the energized tissue-cutting electrode 13 forms a planar cut through the desired tissue bed and allows the probe 11 to readily pass through the tissue. Very little collateral tissue damage at the margins where the tissue cut is made is done by the tissue-cutting electrode 13 as tissue is accessed. The device 10 is preferably advanced through the patient's tissue to the specimen site with the supporting tube 14 in a closed configuration, the supporting tube 14 covering distal extremity 20 of probe 11.

Once the device 10 is in the desired location, the supporting tube 14 can be withdrawn to an opened configuration to expose the distal extremity 20 of the probe 11 by action of the driver (not shown) operatively connected to the arm 28 of collar 27. With the distal extremity 20 of the probe 11 exposed, a vacuum can be generated within the inner lumen 22 of probe 11 by the action of vacuum pump 57. The vacuum generated in the inner lumen 22, acting through the ports 25 in the distal extremity 20 draws tissue at the site against the surface of the distal extremity 20 and holds the tissue against that surface as shown in FIG. 16. The tissue-cutting blade 12 may then be driven distally along with the supporting tube 14 to which the tissue-cutting blade 12 is secured, effective to sever a generally cylindrical shaped tissue specimen 61 from the adjacent tissue site and cover the severed tissue specimen with the supporting tube 14 as shown in FIG. 17.

In preferred embodiments of methods and devices embodying features of the invention, tissue-cutting blade 12 rotates, preferably at high speed, during its distal translation as it severs tissue from the surrounding tissue bed. Such rotation may be in a single rotational direction, or may alternate between clockwise and counter-clockwise rotation. Tissue-cutting blade 12 may also reciprocate longitudinally, with or without rotation, during distal translation as it severs tissue from the surrounding tissue bed. Access cannula 19 acts to protect surrounding tissue from damage during translation, rotation, and/or reciprocation of the supporting tube 14 and tissue-cutting blade 12.

The biopsy device may be removed from the patient after a tissue sample has been collected, and the sample removed for inspection and analysis. The entire device 10 may be removed; however, in preferred embodiments, portions of the device may remain within a patient's body to aid, for example, in the acquisition of further tissue specimens and in the placement of markers at the site from which a tissue sample was taken. For example, the supporting tube 14 and probe 11 may be withdrawn together from within access cannula 19, the supporting tube 14 remaining in a closed configuration outside of probe 11 and helping, along with the vacuum, to hold the tissue sample. Re-introduction of probe 11 and supporting tube 14 within access cannula 19 (which remains in place within a patient's body) allows further samples to be taken. The access cannula 19 serves as a guide for re-introduction of the remainder of the device 10 and aids in obtaining subsequent tissue samples. Alternatively, the probe 11 may be removed, with a tissue sample held by vacuum, from within the supporting tube 14, while supporting tube 14 and access cannula 19 remain in place within the patient's body. Re-introduction of probe 11 within supporting tube 14 allows further samples to be taken.

Such further samples may be from the same location, or from different locations. Where subsequent samples are taken from the same location as a previous sample, so that the tissue-cutting electrode 13 need not be activated (since the pathway to the body location has already been formed), further application of vacuum draws tissue near to the elongated probe, where the tissue may be separated from adjacent body tissue by the tissue-cutting blade 12. Due to the planar cut made by the tissue-cutting electrode 13 through the tissue from which the specimen is to be obtained, the initial cylindrical specimen 61 is typically a split specimen which greatly aids in its evaluation. Although the initial samples are typically split samples, subsequent samples taken from the same location are typically not split samples.

Access cannula 19 exterior to the supporting tube 14 can be left in the patient with its distal end at the site from which the specimen was obtained in order to provide access to the site at a later time. Access cannula 19 may thus be used to allow a marker or other device to be deposited at the site, or to guide further procedures or treatments at the site as necessary or desirable. After the biopsy procedure is completed, the incision formed by the initial cut through the patient's skin may be appropriately closed.

Figures 18, 19:
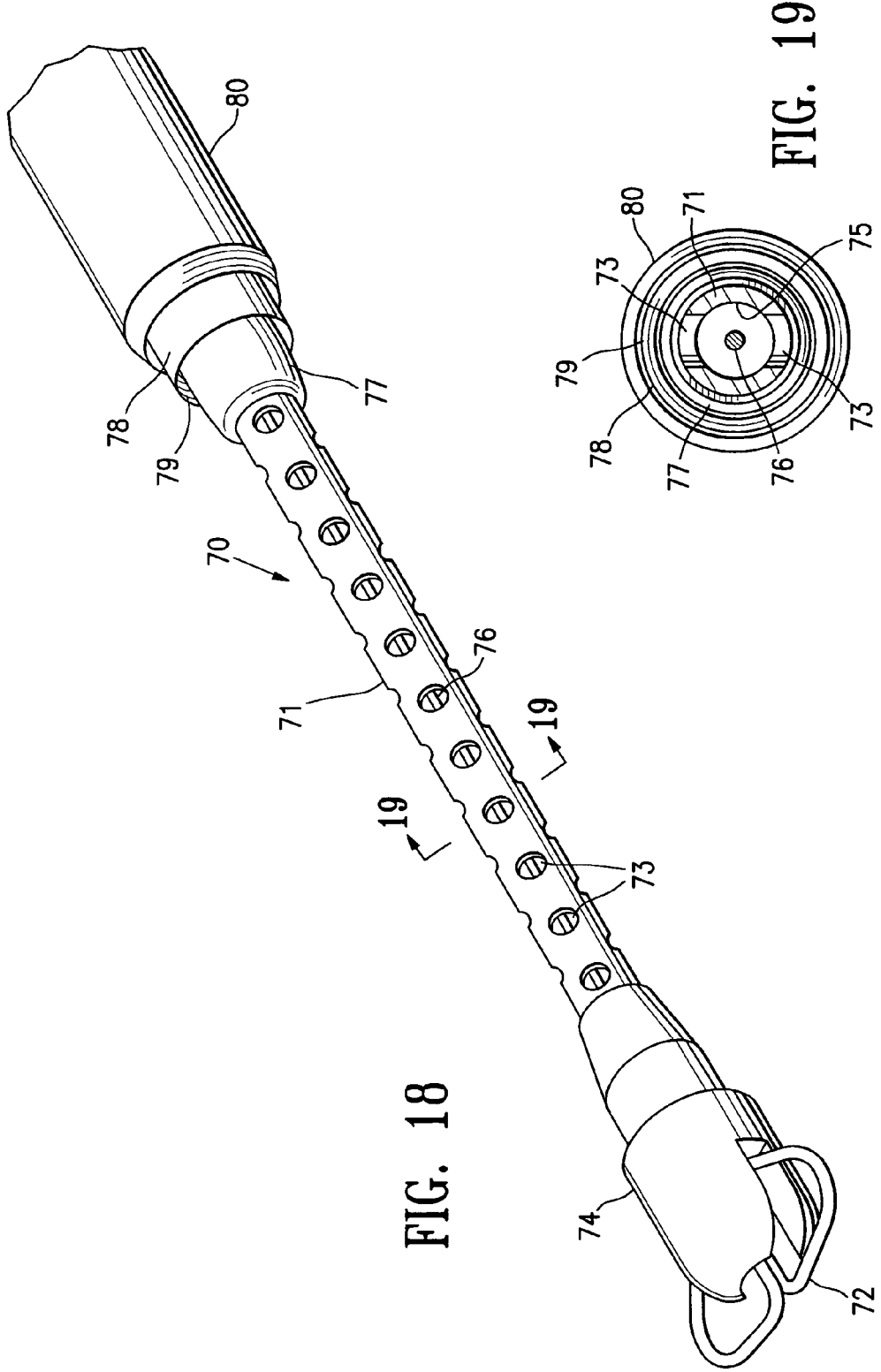
FIG. 18 is a perspective view of an alternative probe member for the biopsy device.
FIG. 19 is a transverse cross-sectional view of the biopsy device shown in FIG. 18 taken along the lines 19—19.

An alternative probe member 70 embodying features of the invention is depicted in FIGS. 18 and 19. In this alternative the distal extremity 71 of the probe device 70 is of tubular construction as shown. The tissue-cutting electrode 72 on the enlarged distal end 74 of the distal extremity 71 of the probe member 70 has an expandable construction which is disclosed in copending application Ser. No. 09/477,255, filed Jan. 4, 2000, entitled Apparatus and Method for Accessing A Biopsy Site, by Burbank et al., which is incorporated herein by reference in its entirety. The tubular distal extremity 71 has a plurality of ports 73 which are in fluid communication with an inner lumen 75. Tissue-cutting electrode 72 is secured to the enlarged distal end 74. A proximal enlargement 77 is disposed proximally of the distal extremity 71 on the probe member 70. An electrical conductor 76 (shown in FIG. 19) extends through inner lumen 75 and is electrically connected to electrode 72. A supporting tube 78 carrying a circular cutter 79 extends about the probe member 70 within access cannula 80. The probe 70 is used with accessing cannula 80, supporting tube 78 and circular tissue-cutting blade 79 in the same manner as described above for the embodiment shown in FIGS. 1–14. The supporting tube 78 may be configured to allow the probe 70 to be withdrawn with the specimen for specimen removal leaving the distal end of the accessing cannula located at the biopsy site.

Figure 20:
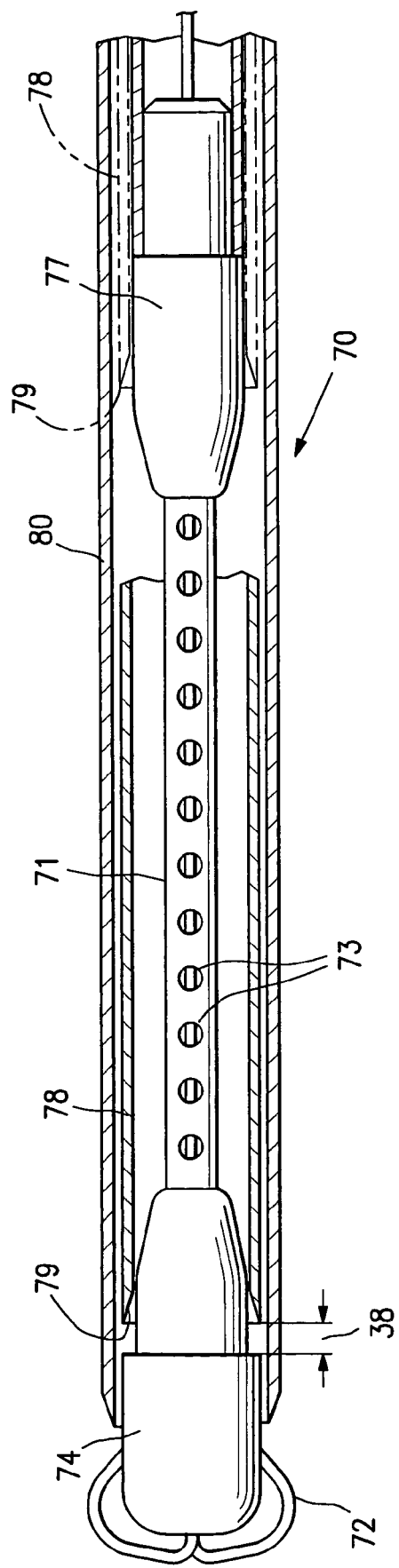
FIG. 20 is a longitudinal cross-sectional view of a device embodying features of the invention as shown in FIG. 18, with the access cannula and supporting tube in a closed configuration.

A cross-sectional view of a device 70 having an expandable tissue-cutting electrode 72 embodying features of the invention is shown in FIG. 20, with the access cannula 80 shown in a closed configuration. Supporting tube 78 circular cutter 79 are shown in a distally-disposed, closed configuration (dark lines) and in a proximally-disposed, open configuration (dotted lines) within access cannula 80, which acts as a sheath to enclose the inner elements of the device 70, particularly when it is in its distally-disposed, closed configuration.

The use of such a device 70 is illustrated in FIGS. 21A–21F, which illustrate a method of using an apparatus for accessing a body site having features of the invention. For example, the apparatus may be first inserted into a patient's body using radiofrequency energy applied via the tissue-cutting electrode; the access cannula and tissue-cutting blade may be retracted, followed by application of vacuum; the tissue-cutting blade and access cannula may be advanced though tissue to cut a sample; the sample may then be removed along with the tissue-cutting blade and tissue-cutting electrode, leaving the access cannula in place; the sample may be removed from the apparatus (with the vacuum turned off) by retracting the supporting tube and tissue-cutting blade; and then the supporting tube, tissue-cutting blade, and tissue-cutting electrode may be re-inserted within the access cannula for removal of further samples.

As illustrated in FIGS. 21A–21F, a first step in obtaining a tissue sample, or in obtaining several tissue samples, from a location within a patient's body, includes inserting a device 70 into a patient's body. A device 70 may be inserted into a patient's body in a configuration as illustrated in FIG. 21A, with distal cutter 72 activated with RF energy to cut through tissue. Access cannula 80 is disposed distally in a closed configuration, with supporting tube 78 and circular cutter 79 proximally disposed in an open configuration within the access cannula 80. Alternatively, supporting tube 78 and circular cutter 79 may be distally disposed within the access cannula 80. If desired, a scalpel or other sharp instrument may be used to make an initial incision through a patient's skin 81; however, the initial incision and subsequent advancement of the device into a patient's body may be done solely using a distal cutter 72 under RF power. In preferred embodiments, the circular cutter 79 and access cannula 80 move together, remaining in the configuration shown in FIG. 21 C.

In a second step, access cannula 80 may be retracted (or probe 71 extended distally into a patient's body tissue) to obtain the configuration illustrated in FIG. 21B. In this configuration, probe 71 extends distally of access cannula 80, circular cutter 79 and supporting tube 78, exposing ports 73 to surrounding tissue. Vacuum, such as may be supplied by a vacuum system with a vacuum source, may be applied via ports 73 to urge tissue into contact with the distal extremity 71 of the probe member 70.

A further step in a method obtaining a tissue sample, or in obtaining several tissue samples, from a location within a patient's body is illustrated in FIG. 21C. Circular cutter 79, followed by access cannula 80, may be advanced into surrounding tissue by distal movement around distal extremity 71 effective to sever tissue from the surrounding tissue bed. This may result in a split tissue sample (split due to the action of distal cutter 72 as device 70 is inserted into a desired location within a patient's body) disposed within supporting tube 78 and preferably held against distal extremity 71 by action of vacuum. Thus, after advancement of the supporting tube and access cannula, as shown in FIG. 21C, a tissue sample is held within device 70 for removal from a patient.

Tissue removal may be performed as illustrated in FIG. 21D. Portions of a device 70, including a distal extremity 71, a supporting tube 78, and a circular cutter 79, and a tissue sample held within supporting tube 78 and circular cutter 79, may be removed proximally by withdrawing them from within an accessing cannula 80, which remains in place at least partially within a patient's body.

The tissue sample may be removed from the device outside the patient's body for investigation, analysis and storage as desired. As shown in FIG. 21E, portions of the device 70 may be configured for removal of a tissue sample by retraction of the supporting tube 78 and circular cutter 79 to expose the tissue sample, and by closing the vacuum connection between ports 73 and a vacuum system with a vacuum source.

The accessing cannula 80 provides a guide for re-insertion of portions of the device 70 that have been removed from the patient, as illustrated in FIG. 21F. The device 70 is shown in FIG. 21F after re-insertion into a patient's body in a configuration for recovery of another tissue sample. As the configuration in FIG. 21F is the same as that in FIG. 21A, it will be understood that subsequent tissue samples may be acquired by steps described above and as illustrated in FIGS. 21B and the following figures. Alternatively, if no further samples are desired, the accessing cannula 80 may be removed after the steps illustrated in FIG. 21E and standard post-operative care provided to the patient.

In addition to suction ports 25, the distal extremity 20 (and optionally the supporting tube 14) may have features configured to retain a tissue sample. For example, a distal extremity 20 may include radial elements configured to engage and retain tissue, such as hooks, barbs, hairs, or probes, that may grab and/or puncture tissue of an adjacent tissue sample. Such radial elements may be angled to be other than perpendicular to a longitudinal axis of probe 11 (e.g., angled to point partially in a distal direction), so that a tissue specimen is retained during distal movement of the probe 11.

In addition, tissue-cutting electrode may be configured to be able to retract or otherwise reduce its radial extent before being removed proximally through supporting tube 14 during recovery of a tissue specimen. Such retraction is effective to reduce the possibility of damage to a tissue-cutting blade 12 as the tissue-cutting electrode 13 is withdrawn. Similarly, the possibility of damage to an access cannula 19 is reduced by retraction of a tissue-cutting electrode 13 before withdrawal of a probe 11 through the access cannula 19. The radial extent of a tissue-cutting electrode 13 may be reduced by, for example, retracting a central supporting portion of a tissue-cutting electrode of the type illustrated in FIG. 18, or by retracting a distal supporting portion of a tissue-cutting electrode of the type illustrated in FIG. 1. Such retraction may be effected by proximal movement of a connecting element attached to such supporting elements. For example, such a connecting element may be, or may be connected to, an electrical conductor 41 or 76.

Those skilled in the art will recognize that various modifications may be made to the specific embodiments illustrated above. In addition, it will be readily appreciated that other types of instruments may be inserted into the tissue site through the supporting tube or a suitable cannula in addition to or in place of the instruments described above. These and other modifications that may suggest themselves are considered to be within the scope of the claims that follow.

What is claimed is:

1. An biopsy system for separation of a tissue specimen from a target tissue site and collection of the separated tissue specimen, comprising:
   a. a handle having a recess in a surface thereof; and
   b. a biopsy device comprising
      i. a housing configured to fit within the recess provided in the housing,
      ii. an elongated probe which has a proximal end disposed within the housing, a distal end, an inner lumen extending within the probe and which has a distal extremity with a plurality of apertures in a wall thereof that is in fluid communication with the inner lumen extending within the probe and with a small transverse dimension less than portions of the probe distal to the distal extremity; and
      iii. a tissue-cutting blade which is at least partially disposed about the elongated probe, which lies in a plane traversing the longitudinal axis of the probe, which has an inner dimension greater than the small transverse dimension of the distal extremity of the probe, and which is secured to a driving member configured for longitudinal movement along a length of the distal extremity of the probe, and iv. a vacuum tube which has an inner lumen, which has a distal end connected in fluid communication with the inner lumen of the probe member and which has a proximal end configured to be secured to a vacuum source.

2. The system of claim 1 wherein the probe has a tissue penetrating electrode on the distal end there.

3. The system of claim 2 wherein the biopsy device has an electrical conductor with a distal end electrically connected to the electrode and a proximal end configured to be electrically connected to a high frequency, electrical power source.

4. The system of claim 2 including a control module which has a high frequency power source configured to be electrically connected to the proximal end of the electrical conductor of the biopsy device.

5. The system of claim 2 wherein the tissue-penetrating electrode has an arcuate shape and has a chord length at least as great as the transverse dimension of the distal end of the probe.

6. The system of claim 5 wherein the tissue-penetrating electrode at least in part lies in a plane which is parallel to a longitudinal axis of the probe.

7. The system of claim 5 wherein the arcuate tissue-cutting electrode has an expanded deployed configuration with a width greater than an outside transverse dimension of the distal end of the probe and a contracted configuration with a width that is equal to or less than an inside transverse dimension of the inner lumen of the outer tubular member.

8. The system of claim 5 wherein the arcuate tissue-cutting electrode is spaced distally of the distal end of the elongated inner probe.

9. The system of claim 1 including a control module which has a vacuum source configured to be connected in fluid communication with the proximal end of the vacuum tube.

10. The system of claim 1 wherein the driving member is configured to be operably connected to a source of mechanical power for imparting longitudinal movement and rotational movement thereto.

11. The system of claim 1 wherein the distal extremity of the probe has a circular transverse cross-sectional shape.

12. The system of claim 1 including a supporting tube which has proximal and distal ends, which has an inner lumen extending therein, which is slidably disposed about the elongated probe member and which is configured to be advanced over the distal extremity and thereby capture any tissue adjacent the distal extremity.

13. The system of claim 12 wherein the tissue-cutting blade is at the distal end of the supporting tube.

14. The system of claim 12 including an accessing cannula disposed around at least part of the supporting tube.

15. The system of claim 1, wherein the driving member for the tissue-cutting blade is configured to reciprocate longitudinally during distal movement around the probe.

16. The system of claim 1 wherein the driving member is configured for longitudinal movement and rotational movement along a length of the distal extremity of the probe.

17. The system of claim 1 where In the vacuum tube is flexible.

* * * * *